(12) United States Patent
Al-Ali

(10) Patent No.: US 8,280,473 B2
(45) Date of Patent: Oct. 2, 2012

(54) PERFUSION INDEX SMOOTHER

(75) Inventor: Ammar Al-Ali, Tustin, CA (US)

(73) Assignee: Masino Corporation, Inc., Irvine, CA (US)

( * ) Notice: Subject to any disclaimer, the term of this patent is extended or adjusted under 35 U.S.C. 154(b) by 1390 days.

(21) Appl. No.: 11/871,620

(22) Filed: Oct. 12, 2007

(65) Prior Publication Data

US 2008/0091093 A1    Apr. 17, 2008

Related U.S. Application Data

(60) Provisional application No. 60/851,346, filed on Oct. 12, 2006.

(51) Int. Cl.
*A61B 5/1455* (2006.01)

(52) U.S. Cl. .......... 600/324; 600/310; 600/323

(58) Field of Classification Search ........... 600/309–344
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |

(Continued)

FOREIGN PATENT DOCUMENTS

EP    0 870 466 A1    10/1998

(Continued)

OTHER PUBLICATIONS

PCT Communication Relating to the Results of the Partial International Search for PCT/US2007/021816, dated Jul. 3, 2008, in 9 pages.
PCT Communication Relating to the Results of the International Search for PCT/US2007/021816, dated Dec. 4, 2008, in 23 pages.

*Primary Examiner* — Eric Winakur
*Assistant Examiner* — Marjan Fardanesh
(74) *Attorney, Agent, or Firm* — Knobbe Martens Olson & Bear LLP

(57) ABSTRACT

An embodiment of the present disclosure seeks to smooth a perfusion index measurement through use of a baseline perfusion index measurement and/or through the use of multiple PI calculations. The combination of the baseline perfusion index measurement reduces an error between a calculated measurement of PI and actual conditions.

6 Claims, 7 Drawing Sheets

U.S. PATENT DOCUMENTS

| | | |
|---|---|---|
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |

| | | | | | |
|---|---|---|---|---|---|
| 7,254,433 B2 | 8/2007 | Diab et al. | | | |
| 7,254,434 B2 | 8/2007 | Schulz et al. | | | |
| 7,272,425 B2 | 9/2007 | Al-Ali | | | |
| 7,274,955 B2 | 9/2007 | Kiani et al. | WO | WO 2006/097866 | 9/2006 |
| 7,280,858 B2 | 10/2007 | Al-Ali et al. | WO | WO 2004/034898 A2 | 4/2007 |
| 2003/0163032 A1 | 8/2003 | Terry | | | |
| 2006/0167362 A1* | 7/2006 | Neumann et al. ............ 600/504 | | | |

FOREIGN PATENT DOCUMENTS

* cited by examiner

PERFUSION INDEX SMOOTHER

PRIORITY CLAIM TO RELATED PROVISIONAL APPLICATIONS

The present application claims priority benefit under 35 U.S.C. §119(e) of U.S. Provisional Application Ser. No. 60/851,346, filed Oct. 12, 2006, entitled "Perfusion Index Smoother," which is incorporated herein by reference.

RELATED CASES

The present application is related to U.S. Pat. Nos. 6,334,065, 6,606,511 and the continuation, continuation-in-part, and divisional applications thereof. The foregoing disclosure is incorporated herein by reference and included in the present filing.

BACKGROUND OF THE DISCLOSURE

1. Field of the Disclosure

The present disclosure relates in general to patient monitoring and in particular to oximeter patient monitors capable of determining perfusion index measurements.

2. Description of the Related Art

Oximeter systems providing measurements of a monitored patient have become the standard of care in many patient care settings, including surgical, post surgical, neonatal, general ward, home care, physical training, and the like. In general, oximeter systems accept one or more noninvasive signals from an optical sensor or probe capable of emitting multiple wavelengths of light into a tissue site and capable of detecting light after attenuated by the tissue site. The optical sensor generally outputs intensity signal data. FIG. 1 illustrates a photoplethysmograph intensity signal 100 output by an oximeter sensor. An oximeter does not directly detect absorption, and hence does not directly measure a standard plethysmograph waveform. However, the standard plethysmograph can be derived by observing that the detected intensity signal 100 is merely an out of phase version of an absorption profile known to one of skill in the art. That is, the peak detected intensity 102, generally corresponds to a minimum absorption, and minimum detected intensity 104, generally corresponds to a maximum absorption. Further, a rapid rise in absorption during an inflow phase of the plethysmograph is reflected in a rapid decline 106 in intensity. Likewise, a gradual decline in absorption during the outflow phase of the plethysmograph is reflected in a gradual increase 108 in detected intensity.

FIG. 2 illustrates a flow calculator 200 which receives a processed signal 202 responsive to at least one of the intensity signals output from the sensor. In an embodiment, the flow calculator outputs an indication of blood flow, such as, for example, a perfusion index (PI) 204. In an embodiment, the PI 204 comprises a relative indication of pulse strength at a monitoring site. For example, the PI 204 may be defined as the ratio of the wavelength's ($\lambda$) AC signal to the DC signal, or the percentage of pulsatile signal to non-pulsatile signal, according to the following:

$$PI = (\lambda_{max} - \lambda_{min})/\lambda_{DC}$$

where $\lambda_{max}$ is the maximum value, $\lambda_{min}$ is the minimum value, and $\lambda_{DC}$ is the average value of the signal 202.

Once calculated, the PI 204 may advantageously be displayed in a wide number of ways, including rising LEDs or other display elements, text, graphics, or other visual elements including color, flashing, and the like, trended data, trace data, or the like. FIG. 3A illustrates a display output for an oximeter patient monitor 302 including a textual PI display 304 (shown as "3.25 PI") ranging from 1.0 to 20. FIG. 3B illustrates a display output for a handheld oximeter patient monitor 322 including a PI bar 324 ranging from, for example, "<0.1%" to ">5%" with steps of "<0.1%," "0.25%," "0.5%," "1%," "1.25%," "1.5%," "1.75%," "2%," "3%," and ">5%." An artisan will recognize from the disclosure herein that various steps and a wide variety of scalars or other mathematical mapping can be used to make PI numbers more readily understandable to a caregiver. However, using the foregoing scale, the PI bar 324 can be used as a diagnostic tool during low perfusion for the accurate prediction of illness severity, especially in neonates. Moreover, the rate of change in the PI bar 324 can be indicative of blood loss, sleep arousal, sever hypertension, pain management, the presence or absence of drugs, or the like. According to one embodiment, a measurement below about "1.25%" may indicate medical situations in need of caregiver attention, specifically in monitored neonates. Because of the relevance of about "1.25%", the PI bar 324 may advantageously include level indicia that switch sides of the PI bar 324, thus highlighting any readings below about that threshold. Moreover, behavior of the PI bar 324, as discussed below, may advantageously draw attention to monitored values below such a threshold.

The PI bar 324 may advantageously activate LEDs from a bottom toward a top such that the bar "fills" to a level proportional to the measured value. In one embodiment, the PI bar 324 shows a static value of perfusion for a given time period, such as, for example, one or more pulses. In another embodiment, or functional setting, the PI bar 324 may advantageously pulse with a pulse rate, may hold the last reading and optionally fade until the next reading, may indicate historical readings through colors or fades, traces or the like. Additionally, the PI bar 324 may advantageously change colors, flash, increasingly flash, or the like to indicate worsening measured values of perfusion.

As discussed above, the monitors 302, 322 may include output functionality that outputs, for example, trend perfusion data, such that a caregiver can monitor measured values of perfusion over time. Alternatively or additionally, the monitors 302, 322 may display historical trace data on an appropriate display indicating the measured values of perfusion over time. In an embodiment, the trend data is uploaded to an external computing device through, for example, a multipurpose sensor connector or other input output systems such as USB, serial or parallel ports, computing networks, or the like. Additional information regarding the calculation and use of PI is disclosed in the '065 patent, assigned to Masimo Corporation ("Masimo") of Irvine, Calif., and incorporated by reference herein.

SUMMARY OF THE DISCLOSURE

Aspects of the present disclosure include a system which provides a more accurate indication of PI. In one embodiment, the wavelength used to determine PI is in the infrared (IR) spectrum. IR wavelengths are more independent of saturation than are wavelengths in the Red (R) spectrum. As a result, when the saturation changes, the PI calculated from a R wavelength tends to vary greater than the PI calculated from a IR wavelength. Although the IR intensity signal data is less responsive to saturation than various other intensity channels, the IR intensity signal remains somewhat susceptible to motion-induced noise, distortion and the like. In general, PI measurements during lower signal quality or distortion generally trends the PI too high. As understood by an artisan from the disclosure herein, higher PI measurements should correlate to better perfusion through the tissue site, and lower PI measurements should correlate to lower perfusion through the tissue site. Thus, noise may cause a patient monitor to give a caregiver the indication that a patient has better perfusion through a measurement site than is actually the case.

Based at least thereon, embodiments of the present disclosure seek to reduce an error between a calculated measurement of PI and actual conditions. In an embodiment, a baseline perfusion index ("baseline PI") is determined and used to improve measurements during motion conditions. For example, a smoother may advantageously determine a baseline PI during strong signal quality, high signal confidence conditions, and use that baseline PI or a statistical combination of baseline PIs instead of or in addition to the current PI that is being influenced by noise. In an embodiment, the smoother selects the lower PI value as the output PI value. This is because motion noise tends to increase PI, thus the lower PI value tends to be the more accurate value.

In an embodiment, PI is calculated using at least two different calculation techniques. The two different calculations are analyzed and a PI indication is determined. In an embodiment, the lower of the two PI values is chosen. In an embodiment, the PI values are averaged or statistically analyzed to determine a more accurate value for PI.

In an embodiment, a method of smoothing a perfusion index measurement in an oximeter system is disclosed. The method includes the steps of establishing a baseline perfusion index during quality signal conditions of a signal responsive to intensity signals acquired from a detector capable of detecting light attenuated by body tissue and leveraging the baseline perfusion index during poor signal conditions. In an embodiment, leveraging includes outputting the baseline perfusion index when a current perfusion index measurement is higher than the baseline perfusion index. In an embodiment, leveraging includes outputting a current perfusion index measurement when the baseline perfusion index is higher than the current perfusion index measurement. In an embodiment, the signal is responsive to an IR intensity signal.

In an embodiment, an oximeter is disclosed. The oximeter includes an input capable of receiving intensity signal data responsive to intensity signals acquired from a detector capable of detecting light attenuated by body tissue, a memory storing a baseline Perfusion Index (PI) and a processor programmed to output the baseline PI when the signal data includes motion-induced noise and a current PI derived from the signal data is not lower than the baseline PI. In an embodiment, an alarm is included which is configured to alert a caregiver when the output meets predetermined criteria. In an embodiment, the processor is programmed to output the current PI when the signal data is relatively calm or when the current PI is lower than the baseline PI.

In an embodiment, a method of determining an indication of perfusion index in a patient monitor is disclosed. The method includes the steps of receiving plethysmographic data, calculating two or more indications of perfusion index using at least two different calculation techniques, and determining a final indication of perfusion index based on the indications of perfusion index. In an embodiment, the final indication of perfusion index is determined by selecting the lowest indication of perfusion index. In an embodiment, the final indication of perfusion index is determined by statistical analysis. In an embodiment, the final indication of perfusion index is determined by averaging the indications of perfusion index.

In an embodiment, a method of determining an indication of perfusion index is disclosed. The method includes the steps of receiving plethysmographic data and determining an indication of perfusion index by utilizing at least one calculation techniques to determine a resulting indication of perfusion index. In an embodiment, determining the indication of perfusion index includes utilizing the calculation technique that will result in the lowest perfusion index value.

In an embodiment, an oximeter is disclosed. The oximeter includes an input capable of receiving intensity signal data responsive to intensity signals acquired from a detector capable of detecting light attenuated by body tissue, a first calculator configured to calculate a first indication of perfusion index using a first calculation technique, a second calculator configured to calculate a second indication of perfusion index using a second calculation technique and a processor configured to utilize at least one of the first and second calculators to determine a resulting indication of perfusion index. In an embodiment, the processor is configured to select the calculator which calculates the lowest indication of perfusion index. In an embodiment, the processor utilizes both calculation techniques. In an embodiment, the processor is further configured to select the lowest indication of perfusion index as the resulting indication of perfusion index.

In an embodiment, a method of determining an indication of a physiological condition using data responsive to intensity signals acquired from a detector capable of detecting light attenuated by body tissue is disclosed. The method includes the steps of determining one or more indications of pulse information from data responsive to intensity signals acquired from a detector capable of detecting light attenuated by body tissue, determining a first indication of amplitude data for a single pulse based on the one or more indications of pulse information, determining a second indication of amplitude data for a plurality of pulses based on the one or more indications of pulse information, determining a final indication of amplitude data based on the first and second indications and outputting the final indication. In an embodiment, the amplitude data is used to determine an indication of perfusion. In an embodiment, determining a final indication includes selecting the lowest indication of amplitude from the first and second indications of amplitude. In an embodiment, determining a final indication includes averaging the first and second indications of amplitude. In an embodiment, determining a final indication is based on a statistical analysis of the first and second indications of amplitude. In an embodiment, the combination includes an averaged combination of pulses. In an embodiment, the combination includes a maximum and minimum amplitude of a plurality of pulses. In an embodiment, the combination includes a statistical combination of pulses.

For purposes of summarizing the disclosure, certain aspects, advantages and novel features of the disclosure have been described herein. Of course, it is to be understood that not necessarily all such aspects, advantages or features will be embodied in any particular embodiment of the disclosure.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit its scope.

DETAILED DESCRIPTION OF THE PREFERRED EMBODIMENT

Figure 1:
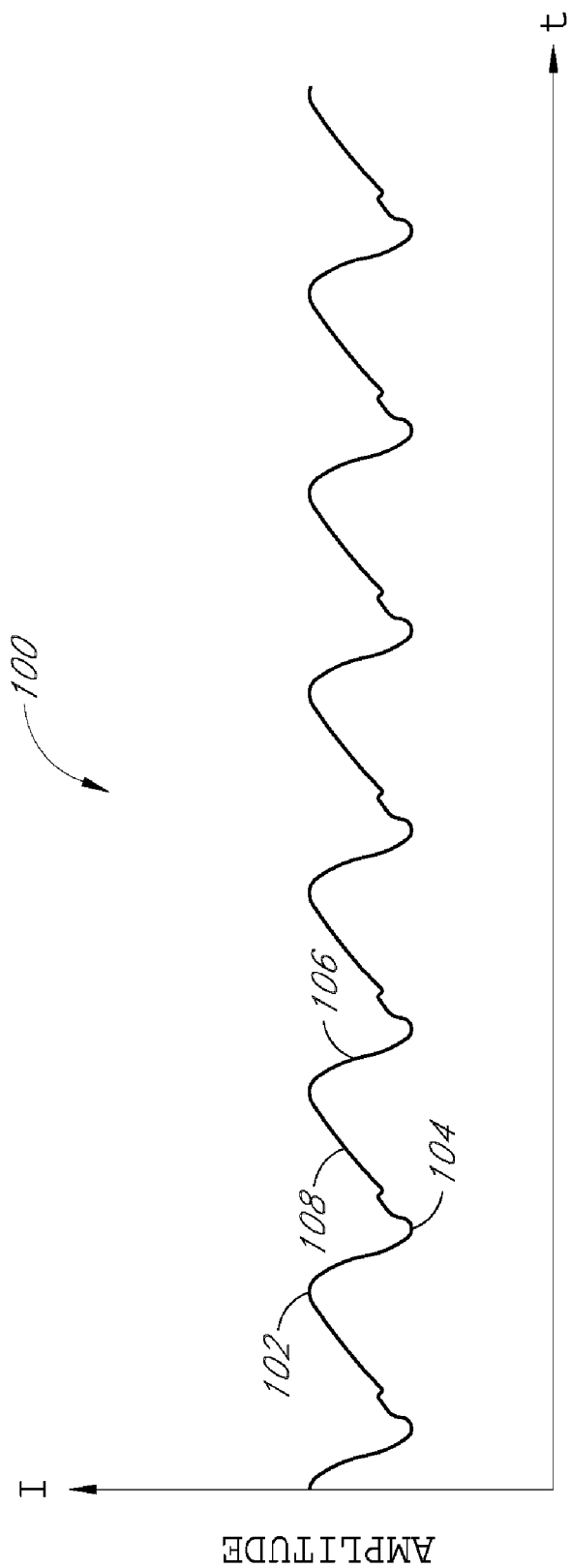
FIG. 1 illustrates a graph showing an intensity "plethysmograph" oximetry waveform.
Figure 3B:
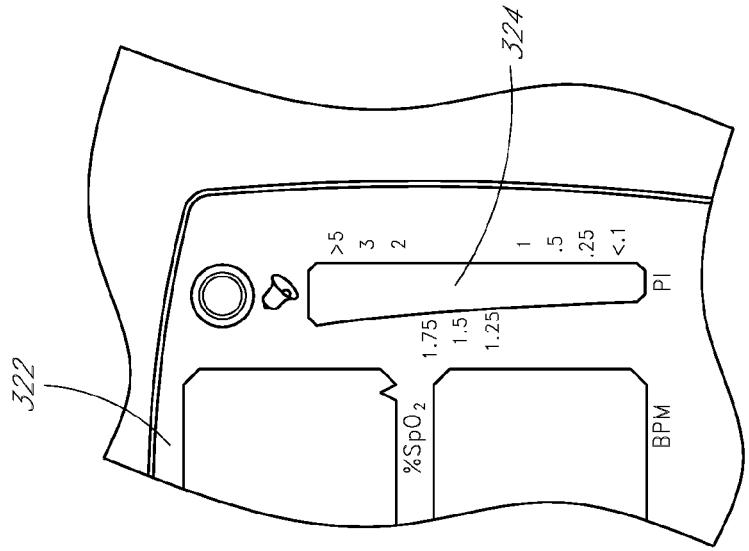
FIGS. 3A-3B illustrate patient monitors capable of calculating and displaying the measurements of FIG. 2.
Figure 2:
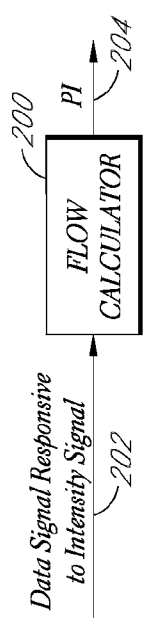
FIG. 2 illustrates a flow calculator capable of determining measurements for a perfusion index.
Figure 3A:
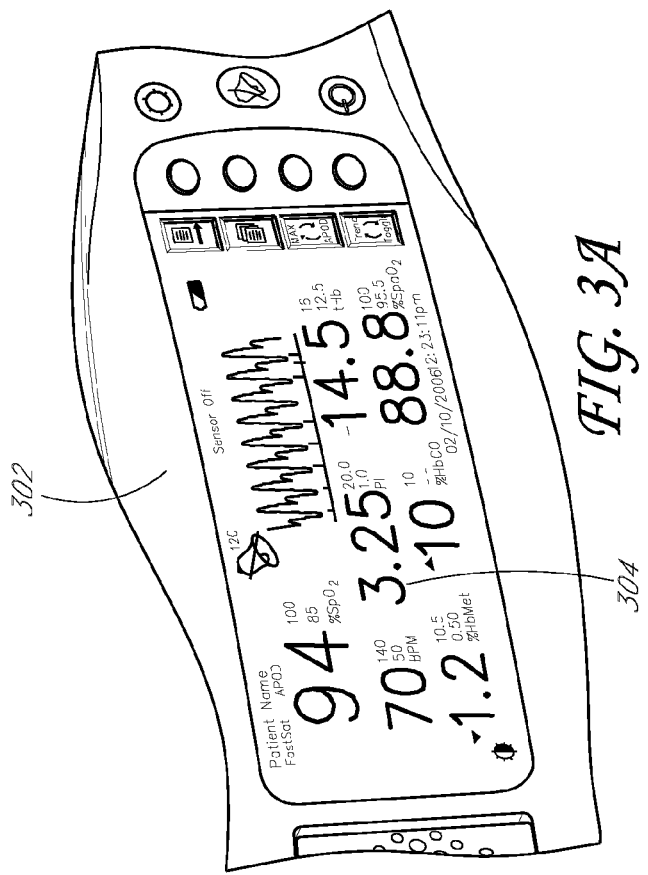
Figure 4:
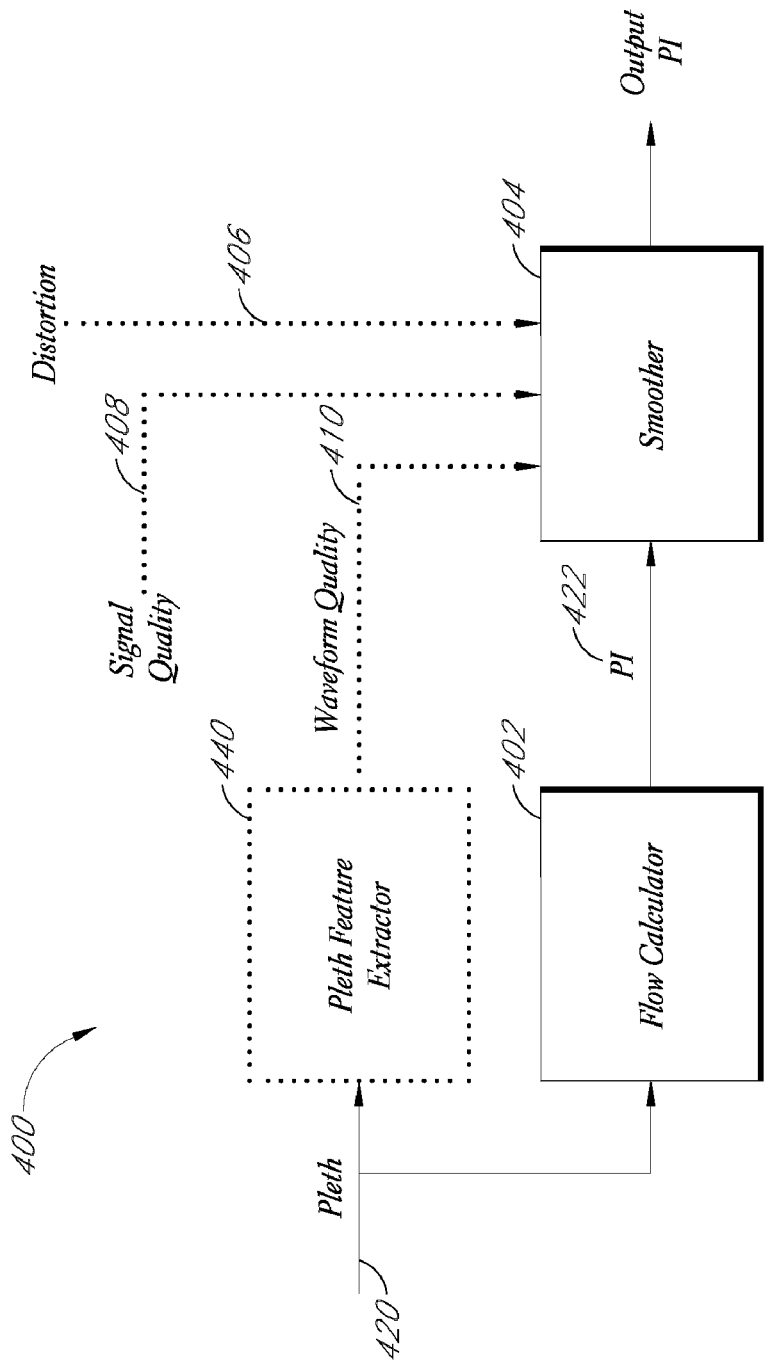
FIG. 4 illustrates a simplified block diagram of a smoothed perfusion index generator, according to an embodiment of the disclosure.

FIG. 4 illustrates a simplified block diagram of a smoothed perfusion index generator 400, according to an embodiment of the disclosure. As shown, the generator 400 includes a flow calculator 402, ad smoother 404 and optional indications of noise, including a measure of distortion 406, signal quality 408, and waveform quality 410. In an embodiment, a data signal 420 responsive to an intensity signal is input into the flow calculator 402, and a current value 422 of PI is calculated. A skilled artisan will recognize a number of calculations that can determine values of perfusion, including, for example, the foregoing ratio of the AC signal to the DC signal. The current value 422 of PI, which in an embodiment is subject to noise and distortion in the data signal 420, is input into the smoother 404, which reduces an error between the current value 422 of PI and actual perfusion conditions. For example, the smoother 404 may advantageously determine a baseline PI, and depending upon an indication of some or all of an amount of distortion, noise, signal quality, and/or waveform quality in the data signal 422, substitute or combine the baseline PI for or with the current value 422 to generate an output PI 430.

In an embodiment, the wavelength used to determine PI is in the infrared (IR) spectrum. IR wavelengths are more independent of saturation than are wavelengths in, for example, the Red (R) spectrum. As a result, when the saturation changes, the PI calculated from a R wavelength tends to vary greater than the PI calculated from a IR wavelength.

In an embodiment, the distortion signal 406 may comprise a Boolean value indicating whether the data signal 422 includes, for example, motion-induced noise. Although an artisan will recognize from the disclosure herein a number of methodologies for deriving the distortion signal 406, derivation of a Boolean distortion signal is disclosed in U.S. Pat. No. 6,606,511, incorporated herein by reference. Alternatively, or in addition to, the signal quality signal 408 may comprise a Boolean value indicating whether the data signal 422 meets various waveform criteria Although an artisan will recognize from the disclosure herein a number of methodologies for deriving the signal quality signal 408, derivation of a Boolean distortion signal is disclosed in the '511 patent. Alternatively, or in addition to, a feature extractor 440 may advantageously produce waveform quality outputs 410, indicative of waveform quality or waveform shape. Although an artisan will recognize from the disclosure herein a number of methodologies for deriving the waveform quality signal 410, derivation thereof is disclosed in the '065 patent.

Thus, the smoother 404 accepts one or more or different indicators of the quality of the data signal 420, and determines how to smooth the PI output to reduces errors between data trends and actual perfusion conditions. In an embodiment, the smoothing may advantageously comprise statistical weighting, other statistical combinations, or simply passing the PI 422 through to the output, depending upon one or more of the quality signals 406, 408, 410, or logical combinations thereof. In an embodiment, the smoother 404 selects the lowest PI value to pass to the output PI 422. This is because motion noise tends to increase PI, thus the lower PI value tends to be the more accurate value.

Upon the output of a smoothed PI measurement, a monitor may advantageously audibly and/or visually presents the measurement to a caregiver, and when the measurement meets certain defined thresholds or behaviors, the monitor may advantageously audibly and/or visually alert the caregiver. In other embodiments, the monitor may communicate with other computing devices to alert the caregiver, may compare longer term trend data before alarming, or the like.

Figure 5:
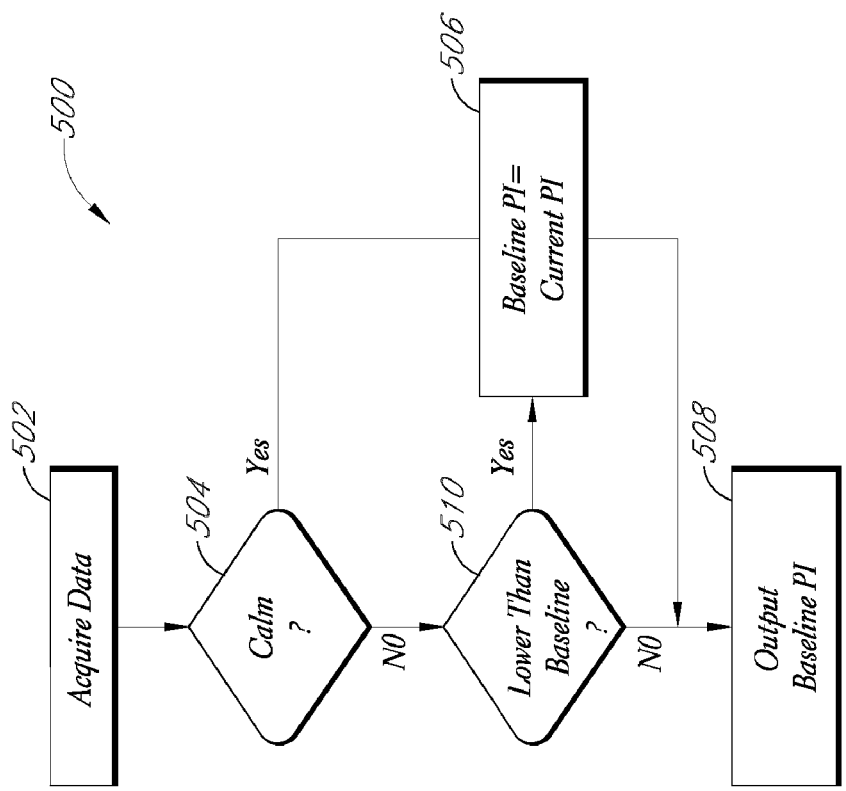
FIG. 5 illustrates a flow chart of a smoothing process, according to an embodiment of the disclosure.

FIG. 5 illustrates a flow chart of a smoothing process 500, according to an embodiment of the disclosure. In block 502, data is acquired responsive to one or more of multiple channel intensity signals. In block 504, a determination is made whether distortion is present, whether signal quality is good, whether there is motion-induced-noise or the like. When acceptable noise levels exist, in block 506, the baseline PI becomes the current PI and in block 508, the baseline PI is output. However, when unacceptable signal quality or the like is detected, the current PI is compared to the baseline PI. When the current PI is smaller than the baseline PI, in block 506, the baseline PI becomes the current PI. However, when the current PI is greater than or equal to the baseline PI, the baseline PI is output in block 510. Thus, the smoothing process 500 determines when a baseline PI can be acquired in quality monitoring conditions, and then uses that baseline PI to avoid drift or other errors that may deteriorate the accuracy of the PI output. An artisan will recognize from the disclosure herein that the baseline PI could be reset periodically, some or all iterations, when other occurrences or measurements suggest a reinitialization, when various trends occur, or the like.

Figure 6:
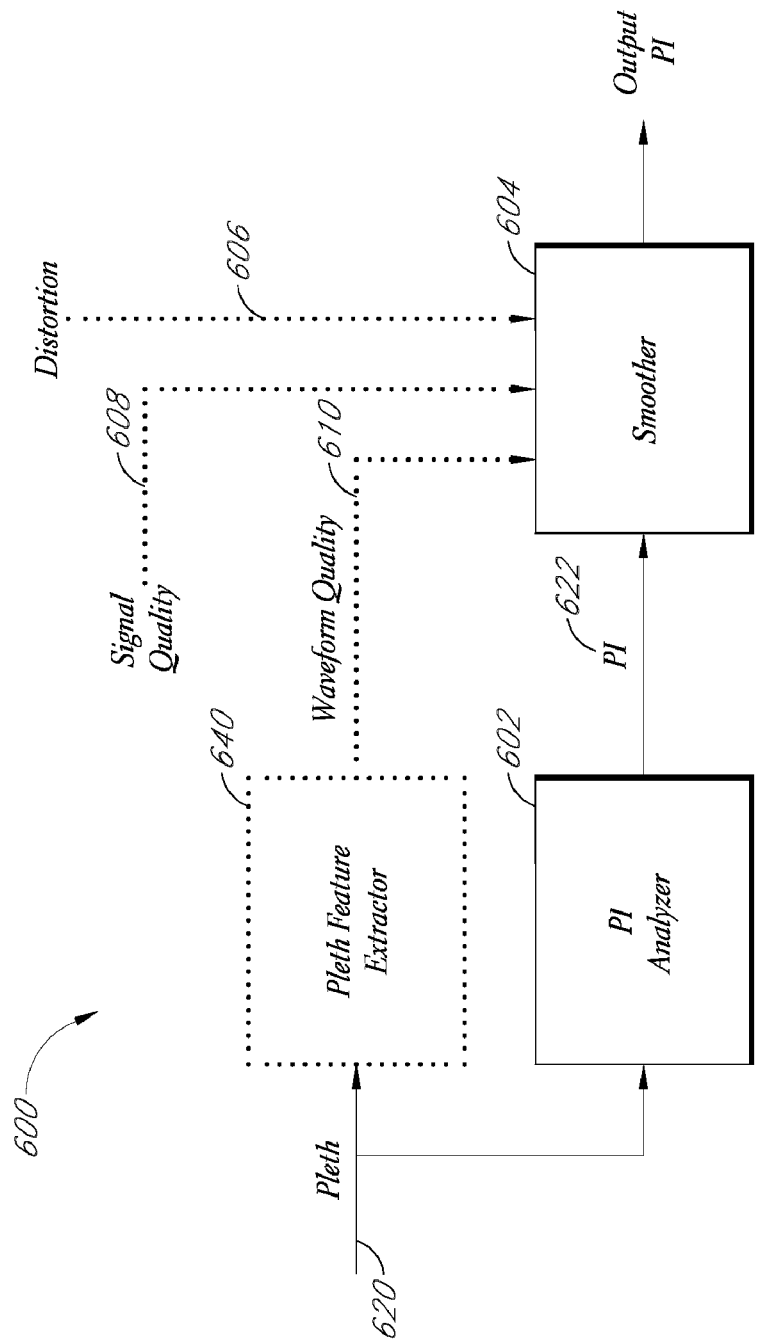
FIG. 6 illustrates another embodiment of a simplified block diagram of a smoothed perfusion index generator.

FIG. 6 illustrates another embodiment of a simplified block diagram of a smoothed perfusion index generator 600. As shown, the generator 600 includes a smoother 604 and optional indications of noise, including a measure of distortion 606, signal quality 608, waveform quality 610, and Pleth Feature Extractor similar to those described with respect to FIG. 4. In an embodiment, a data signal 620 responsive to an intensity signal is input into the PI Analyzer 602, and a PI value 422 is outputted for use by the smoother 604. In an embodiment, the PI Analyzer employs multiple different calculation techniques to determine a more accurate indication of PI. In an embodiment, based on the indications of distortion signal quality, waveform quality and/or other indications of signal quality, a specific calculation technique is used to determine a PI output value 622.

Figure 7:
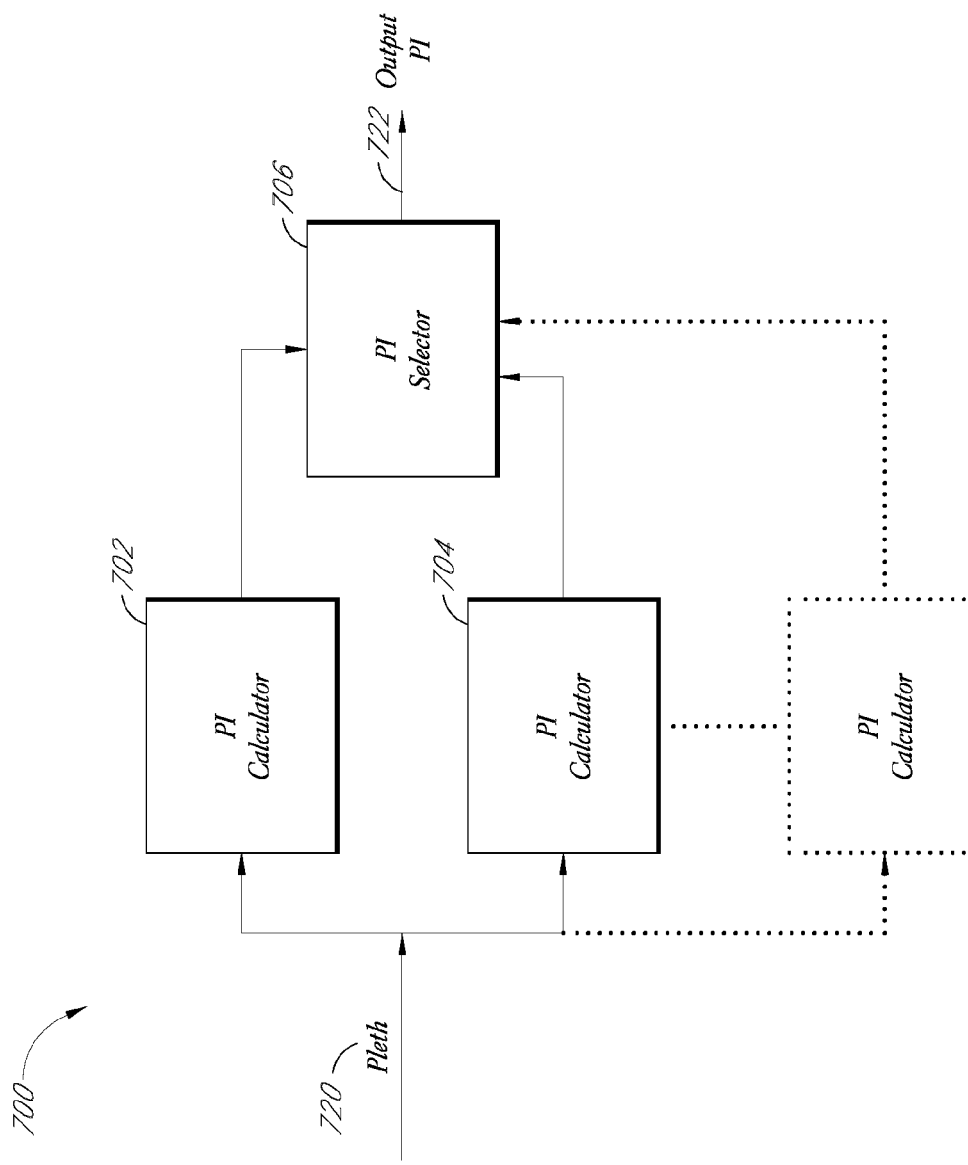
FIG. 7 illustrates a simplified block diagram of an embodiment of a PI determination system using multiple PI calculation techniques.

FIG. 7 illustrates a simplified block diagram of an embodiment of a PI determination system 700 using multiple PI calculation techniques. As shown, pleth data 720 is input into the system. The pleth data 720 is then routed to at least two different PI calculators 702, 704. In an embodiment, more than two different types of calculation techniques can be used. The at least two PI calculators 702, 704 output PI indications for input into the PI selector 706. The PI selector 706 determines a PI value to output. In an embodiment, the PI selector chooses the lowest PI value. In general, the lower PI value should be the more accurate value, particularly in the presence of motion induced noise. This is because motion induced noise tends to raise PI values. In an embodiment, the PI selector 706 averages or otherwise analyzes the PI values using statistical modeling in order to determine a more accurate value of PI.

In an embodiment, one of the PI calculators 702, 704 determines a PI value based on pulse by pulse determination of PI, such as, for example, using the following PI formula as described above:

$$PI=(\lambda_{max}-\lambda_{min})/\lambda_{DC}$$

In an embodiment, one of the PI calculators 702, 704 determines a PI value based on a fixed or variable interval of pleth data including more than one pulse, in effect calculating a bulk PI.

Figure 8:
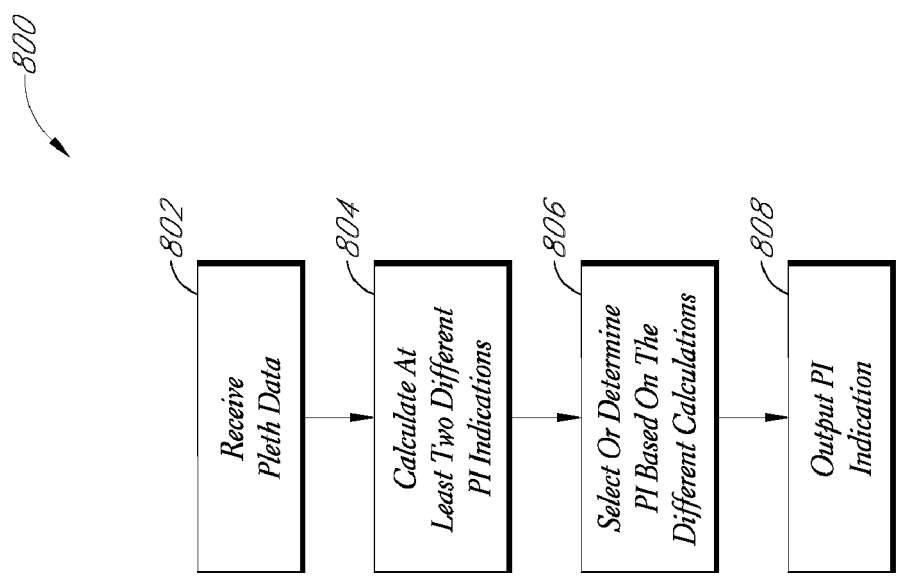
FIG. 8 illustrates a flow chart of a PI decision process, according to another embodiment of the disclosure.

FIG. 8 illustrates a flow chart of a PI decision process 800, according to another embodiment of the disclosure. At block 802, the process 800 receives pleth data 802. The process then moves to block 804 where the process 800 calculates at least two different PI indications, such as, for example, as described with respect to FIG. 7. The process 800 then moves to block 806 where an indication of PI is determined based on the different calculations, again, such as, for example, as described with respect to FIG. 7. The process 800 then repeats itself for each PI value determination.

While the above perfusion index determination system has been described in certain embodiments herein, other embodiments of the present disclosure will be known to those of skill in the art from the descriptions herein. Moreover, the described embodiments have been presented by way of example only, and are not intended to limit the scope of the disclosure. Moreover, those of skill in the art understand that information and signals can be represented using a variety of different technologies and techniques. For example, data, instructions, commands, information, signals, bits, symbols, and chips that can be referenced throughout the above description may be represented by voltages, currents, electromagnetic waves, magnetic fields or particles, optical fields or particles, or any combination thereof.

Those of skill in the art further appreciate that the various illustrative logical blocks, modules, circuits, and algorithm steps described in connection with the embodiments disclosed herein can be implemented as electronic hardware, computer software, or combinations of both. To illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or other form of storage medium known in the art. A storage medium is coupled to the processor, such that the processor can read information from, and write information to, the storage medium. In the alternative, the storage medium can be integral to the processor. The processor and the storage medium can reside in an ASIC. The ASIC can reside in a user terminal, physiological monitor and/or sensor. The processor and the storage medium can reside as discrete components in a user terminal, physiological monitor and/or sensor.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Moreover, it is contemplated that various aspects and features of the disclosure described can be practiced separately, combined together, or substituted for one another, and that a variety of combination and subcombinations of the features and aspects can be made and still fall within the scope of the disclosure. Furthermore, the systems described above need not include all of the modules and functions described in the preferred embodiments. Accordingly, the present disclosure is not intended to be limited by the recitation of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A method performed on a processor of smoothing a perfusion index measurement displayed in an oximeter system, the method comprising:
    establishing a baseline perfusion index during quality signal conditions of a signal responsive to intensity signals acquired from a detector capable of detecting light attenuated by body tissue, and
    displaying a single value of perfusion index, the single value being the baseline perfusion index if a current signal includes motion-induced noise and a current PI derived from the current signal is not lower than the baseline PI, otherwise the single value being the current perfusion index.

2. The method of claim 1, comprising triggering an alarm configured to alert a caregiver when said signal meets predetermined criteria.

3. The method of claim 1, wherein establishing a baseline perfusion index comprises a calculation utilizing a plurality of perfusion indices.

4. The method of claim 1, wherein the signal is responsive to an IR intensity signal.

5. An oximeter comprising:
    an input capable of receiving intensity signal data responsive to intensity signals acquired from a detector capable of detecting light attenuated by body tissue,
    a memory storing a baseline Perfusion Index (PI); and a processor programmed to display a single value of PI, said single value being said baseline PI if a current signal data includes motion-induced noise and a current PI derived from said current signal data is not lower than said baseline PI, otherwise said single value being said current PI.

6. The oximeter of claim 5, comprising an alarm configured to alert a caregiver when said signal data meets predetermined criteria.

* * * * *

UNITED STATES PATENT AND TRADEMARK OFFICE
CERTIFICATE OF CORRECTION

| | |
|---|---|
| PATENT NO. | : 8,280,473 B2 |
| APPLICATION NO. | : 11/871620 |
| DATED | : October 2, 2012 |
| INVENTOR(S) | : Ammar Al-Ali |

It is certified that error appears in the above-identified patent and that said Letters Patent is hereby corrected as shown below:

Title page (Item 73) Assignee, Line 1, change "Masino" to --Masimo--.

Signed and Sealed this
Twenty-second Day of October, 2013

Teresa Stanek Rea
*Deputy Director of the United States Patent and Trademark Office*